United States Patent
Ang et al.

(10) Patent No.: US 10,869,804 B2
(45) Date of Patent: Dec. 22, 2020

(54) METHOD AND SYSTEM FOR USING HAPTIC DEVICE AND BRAIN-COMPUTER INTERFACE FOR REHABILITATION

(71) Applicant: AGENCY FOR SCIENCE, TECHNOLOGY AND RESEARCH, Singapore (SG)

(72) Inventors: Kai Keng Ang, Singapore (SG); Cuntai Guan, Singapore (SG); Kok Soon Phua, Singapore (SG); Longjiang Zhou, Singapore (SG); Chuan Chu Wang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 627 days.

(21) Appl. No.: 15/328,010

(22) PCT Filed: Jul. 23, 2015

(86) PCT No.: PCT/SG2015/050227
§ 371 (c)(1),
(2) Date: Jan. 20, 2017

(87) PCT Pub. No.: WO2016/013980
PCT Pub. Date: Jan. 28, 2016

(65) Prior Publication Data
US 2017/0181915 A1    Jun. 29, 2017

(30) Foreign Application Priority Data
Jul. 23, 2014   (SG) .......................... 10201404337Y

(51) Int. Cl.
*A61H 1/02*   (2006.01)
*A61B 5/11*   (2006.01)
(Continued)

(52) U.S. Cl.
CPC ......... *A61H 1/0274* (2013.01); *A61B 5/0476* (2013.01); *A61B 5/0482* (2013.01);
(Continued)

(58) Field of Classification Search
CPC .. A61H 1/0274; A61B 5/0476; A61B 5/0482; A61B 5/1121; A61B 5/1126
See application file for complete search history.

(56) References Cited

U.S. PATENT DOCUMENTS

| 2008/0300521 | A1 | 12/2008 | Karkanias et al. |
| 2013/0138011 | A1 | 5/2013 | Ang et al. |
| 2014/0018694 | A1* | 1/2014 | Ang ................... A61B 5/04017 600/544 |

FOREIGN PATENT DOCUMENTS

| WO | WO 2005/074371 A2 | 8/2005 |
| WO | WO-2005074371 A2 * | 8/2005 | ............... A61B 5/16 |

OTHER PUBLICATIONS

PCT Notification of Transmittal of the International Search Report and the Written Opinion of the International Searching Authority, or the Declaration for PCT Counterpart Application No. PCT/SG2015/050227, 13 pp., (dated Oct. 9, 2015).
(Continued)

*Primary Examiner* — Christopher D. Prone
*Assistant Examiner* — Christine L Nelson
(74) *Attorney, Agent, or Firm* — Womble Bond Dickinson (US) LLP

(57) ABSTRACT

A method for calibrating and executing a rehabilitation exercise for a stroke-affected limb of a stroke patient is disclosed, the method comprising the steps of providing a haptic device for an able limb of the stroke patient to manipulate to perform a calibration action to result in a first position of the haptic device, and providing the haptic device for the stroke-affected limb to manipulate to perform the calibration action to result in a second position of the haptic
(Continued)

device. The method further comprises the steps of moving the haptic device coupled with the stroke-affected limb from the second position towards the first position until a predetermined counterforce is detected, indicating an extreme position for the stroke-affected limb using the haptic device, and calibrating the haptic device with the extreme position such that during the rehabilitation exercise, the haptic device is prevented from moving beyond the extreme position.

18 Claims, 12 Drawing Sheets

(51) Int. Cl.
| | |
|---|---|
| *A61B 5/22* | (2006.01) |
| *A61B 5/0482* | (2006.01) |
| *G06F 3/01* | (2006.01) |
| *A61B 5/0476* | (2006.01) |
| *G09B 5/06* | (2006.01) |
| *A61B 5/00* | (2006.01) |

(52) U.S. Cl.
CPC .......... *A61B 5/1121* (2013.01); *A61B 5/1126* (2013.01); *A61B 5/225* (2013.01); *A61H 1/02* (2013.01); *A61H 1/0285* (2013.01); *A61H 1/0288* (2013.01); *G06F 3/014* (2013.01); *G06F 3/015* (2013.01); *G06F 3/016* (2013.01); *G09B 5/06* (2013.01); *A61B 5/7475* (2013.01); *A61B 2560/0223* (2013.01); *A61H 2001/0203* (2013.01); *A61H 2201/1635* (2013.01); *A61H 2201/1671* (2013.01); *A61H 2201/5043* (2013.01); *A61H 2201/5048* (2013.01); *A61H 2201/5061* (2013.01); *A61H 2201/5064* (2013.01); *A61H 2230/105* (2013.01)

(56) References Cited

OTHER PUBLICATIONS

Olivier Lambercy, et al., "A Haptic Knob for Rehabilitation of Hand Function", IEEE Transactions on Neural Systems and Rehabilitation Engineering, vol. 15, No. 3, pp. 356-366, (Sep. 2007).

PCT Notification of Transmittal of International Preliminary Report on Patentability for PCT Counterpart Application No. PCT/SG2015/050227; dated Jan. 24, 2017; 6 pp.

\* cited by examiner

METHOD AND SYSTEM FOR USING HAPTIC DEVICE AND BRAIN-COMPUTER INTERFACE FOR REHABILITATION

CROSS-REFERENCE TO RELATED APPLICATIONS

The present application is a U.S. National Phase Application under 35 U.S.C. § 371 of International Application No. PCT/SG2015/050227, filed Jul. 23, 2015, entitled A METHOD AND SYSTEM FOR USING HAPTIC DEVICE AND BRAIN-COMPUTER INTERFACE FOR REHABILITATION, which claims priority to Singapore Patent Application No. 10201404337Y, filed Jul. 23, 2014.

TECHNICAL FIELD

The following discloses a method and system for using a haptic device and a brain computer interface (BCI) for rehabilitation purposes. In particular, to rehabilitate stroke patients.

BACKGROUND ART

Haptic knobs with brain-computer interface (BCI) systems aid stroke patients with arm or hand paralysis in the rehabilitation process. BCI systems use electroencephalogram (EEG) based motor imagery to detect the patient's thinking abilities which control motor movement, while the haptic knob functions as a haptic-assisted device which specifically trains the opening/closing of the paralyzed hand with intensive repetitions.

Prior to the commencement of the rehabilitation, the mechanics of the haptic knob is usually calibrated by a therapist. This is an important step as this determines the movement or range of movement of the haptic knob when rehabilitating the stroke-affected or paralyzed hand. The therapist typically begins by manually moving the patient's stroke-affected hand to assess the range of movement the patient is capable of performing. Based on the results of this exercise, and applying his/her experience, the therapist then enter values into a computer to configure the haptic knob.

The drawback with this is that the calibration process is essentially a manual one, with the accuracy of the calibration largely determined on how experienced the therapist is. Further, it is prone to human error as the therapist would have to essentially translate the results of the exercise into calibration values. Any miscalibration of the haptic knob would have very undesirable results. An under-calibrated haptic knob will result in the rehabilitation exercises being largely ineffective as the range of motion of the patient's stroke-affected hand during the rehabilitation exercises will be under-stressed or under-taxed and as such, there would be little improvement on the patient's disability. On the other hand, an over-calibrated haptic knob will result in excruciating pain on the patient's part as his stroke-affected hand would be overstressed or overtaxed.

Thus, there is a want for a method and system which is able to more effectively and more accurately calibrate the range of movement of the haptic knob.

Another drawback with current haptic knobs-BCI systems is that the assistive forces that the haptic knob applies, to aid the patient in moving the stroke-affected hand during the rehabilitation exercises, do not factor in the actual hand strength of a patient nor the patient's motor imagery score. In other words, the assistive force applied by the haptic knob is not cognizant of either the hand strength or motor imagery ability of the patient, which means that the assistive force is not tailored to the actual capability of the patient. Furthermore, when the hand strength used by a patient is excessive, current haptic knobs in the art do not provide a resistive force to restrict the movement of the stroke-affected hand to incite greater effort from the patient.

Thus, there is a want for a haptic knob that is capable of applying an assistive force that takes into account the hand strength and motor imagery ability of the patient, and is also able to provide a resistive force as well during the rehabilitation exercises.

Furthermore, other desirable features and characteristics will become apparent from the subsequent detailed description and the appended claims, taken in conjunction with the accompanying drawings and this background of the disclosure.

SUMMARY OF INVENTION

According to an aspect of the invention, a method for calibrating and executing a rehabilitation exercise for a stroke-affected limb of a stroke patient is disclosed, the stroke patient having an able limb. The method comprising the steps of providing a haptic device for the able limb to manipulate; providing with an interface, automated visual/audio instructions to guide the stroke patient in using the able limb to manipulate the haptic device to perform at least one calibration action; and determining a first position of the haptic device, the first position resultant from the manipulation of the haptic device by the able limb in completing the at least one calibration action. The method further comprises the steps of providing the haptic device for the stroke-affected limb to manipulate; providing with the interface, automated visual/audio instructions to guide the stroke patient in using the stroke-affected limb to manipulate the haptic device to perform the at least one calibration action; and determining a second position of the haptic device, the second position resultant from the manipulation of the haptic device by the stroke-affected limb in completing the at least one calibration action. The method further comprises the steps of moving the haptic device coupled with the stroke-affected limb from the second position towards the first position until a predetermined counterforce emanating from the stroke-affected limb is detected, indicating an extreme position for the stroke-affected limb using the haptic device; and calibrating the haptic device with the extreme position such that during the rehabilitation exercise for the stroke-affected limb, the haptic device is prevented from moving beyond the extreme position.

Preferably, the rehabilitation exercise has the same sequence of movements as the at least one calibration action.

Preferably, the at least one calibration action is any one of, or any combination of the following actions: finger flexion, finger extension, forearm pronation and forearm supination.

Preferably, the method further comprises the steps of providing with the interface, automated visual/audio instructions to guide the stroke patient in using the able limb to apply maximum strength when the haptic device is stationary; and determining the maximum limb strength of the able limb by measuring the maximum strength applied by the able limb.

Preferably, the predetermined counterforce is greater than one quarter of the maximum limb strength of the able limb.

Preferably, the method further comprises the step of determining a limb strength of the stroke-affected limb by measuring the driving motor current necessary to maintain the same servo motor position during the rehabilitation exercise for the stroke-affected limb.

Preferably, the method further comprises the step of using a brain computer interface (BCI) system to obtain electroencephalogram (EEG) data from the brain of the stroke patient, and determining from the EEG data, a motor imagery score of the stroke patient.

Preferably, the method further comprises the step of executing the rehabilitation exercise for the stroke-affected limb by applying a force with the haptic device.

Preferably, the force applied by the haptic device is a function of the motor imagery score of the stroke patient, the limb strength of the stroke-affected limb and the maximum limb strength of the able limb.

Preferably, the force applied by the haptic device is represented by the equation $$\alpha = -\tanh\left(\frac{5}{h_{max}}\left(h - \frac{h_{max}}{2}\right)\right)\tanh\left(\frac{5m}{m_{max}}\right),$$

wherein $\alpha$ is the force applied by the haptic device, h is the limb strength of the stroke-affected limb, $h_{max}$ is the maximum limb strength of the able limb, m is the motor imagery score of the stroke patient, and $m_{max}$ is a maximum motor imagery score.

Preferably, the force applied by the haptic device is an assistive force or a resistive force depending on the limb strength of the stroke-affected limb.

Preferably, the method further comprises the step of using the EEG data to compute a Temporal Spectral-dependent Brain Index (TSBI), and then plotting the TSBI against Fugi-Meyer Score Improvement in a graph so as to predict the progress of stroke rehabilitation.

Preferably, the TSBI is calculated using the equation:

$$TSBI(t) = \frac{1}{n_k} \sum_{n=k_1}^{k_2} \left| \frac{R_n^*(t) - L_n^*(t)}{R_n^*(t) + L_n^*(t)} \right|$$

According to another aspect of the invention, a system for calibrating and executing a rehabilitation exercise for a stroke-affected limb of a stroke patient is disclosed, the stroke patient having an able limb. The system comprises a haptic device, an interface, at least one sensor and a processor. Wherein the haptic device is capable of being manipulated by the able limb, in response to automated visual/audio instructions provided by the interface to guide the stroke patient in using the able limb to manipulate the haptic device to perform at least one calibration action, wherein the at least one sensor is configured to determine a first position of the haptic device, the first position resultant from the manipulation of the haptic device by the able limb in completing the at least one calibration action. Wherein the haptic device is also capable of being manipulated by the stroke-affected limb, in response to automated visual/audio instructions provided by the interface to guide the stroke patient in using the stroke-affected limb to manipulate the haptic device to perform the at least one calibration action; wherein the at least one sensor is configured to determine a second position of the haptic device, the second position resultant from the manipulation of the haptic device by the stroke-affected limb in completing the at least one calibration action. Wherein the haptic device is also capable of moving, coupled with the stroke-affected limb, from the second position towards the first position until a predetermined counterforce emanating from the stroke-affected limb is detected by the least one sensor, indicating an extreme position for the stroke-affected limb using the haptic device. Wherein the processor is configured to calibrate the haptic device with the extreme position such that during the rehabilitation exercise for the stroke-affected limb, the haptic device is prevented from moving beyond the extreme position.

Preferably, the haptic device is a robotic device and is shaped in the form of a glove or a knob.

Preferably, the at least one sensor comprises position encoders for providing position and orientation data of the haptic device.

Preferably, the system further comprises a brain computer interface (BCI) system, the BCI system configured to obtain electroencephalogram (EEG) data from the brain of the stroke patient, and determine from the EEG data a motor imagery score of the stroke patient.

Preferably, the haptic device is configured to execute the rehabilitation exercise by applying a force during the rehabilitation exercise for the stroke-affected limb, wherein the force is a function of the motor imagery score of the stroke patient, a limb strength of the stroke-affected limb and a maximum limb strength of the able limb.

Preferably, the force applied by the haptic device is an assistive force or a resistive force depending on the limb strength of the stroke-affected limb.

Preferably, the EEG data is used to compute a Temporal Spectral-dependent Brain Index (TSBI), and the TSBI is then plotted against Fugi-Meyer Score Improvement in a graph so as to predict the progress of stroke rehabilitation.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments, by way of example only, and to explain various principles and advantages in accordance with a present embodiment.

Skilled artisans will appreciate that elements in the figures are illustrated for simplicity and clarity and have not necessarily been depicted to scale. For example, the dimensions of some of the elements in the block diagrams or steps in the flowcharts may be exaggerated in respect to other elements to help improve understanding of the present embodiment.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the preferred embodiments to disclose a method and system which is able to effectively and accurately calibrate the haptic device. Furthermore, the extreme positions for the stroke-affected hand when using the haptic device can be automatically and accurately determined, enhancing the effectiveness of the rehabilitation exercises and avoiding excruciating pain for the patient. The disclosed method and system is fully automated and does not rely on the manual calibration of a therapist which is subject to human error.

Further, in accordance with the present embodiments, during the execution of the rehabilitation exercises, the haptic device takes into account the maximum hand strength of the able hand, the hand strength of the stroke-affected hand and motor imagery ability of the patient when applying an assistive force as well as a resistive force during the rehabilitation exercises. Further still, in accordance with the present embodiments, the electroencephalogram (EEG) data can be used to predict the progress of the stroke rehabilitation. While exemplary embodiments have been presented in the foregoing detailed description of the invention, it should be appreciated that a vast number of variations exist.

Figure 1:
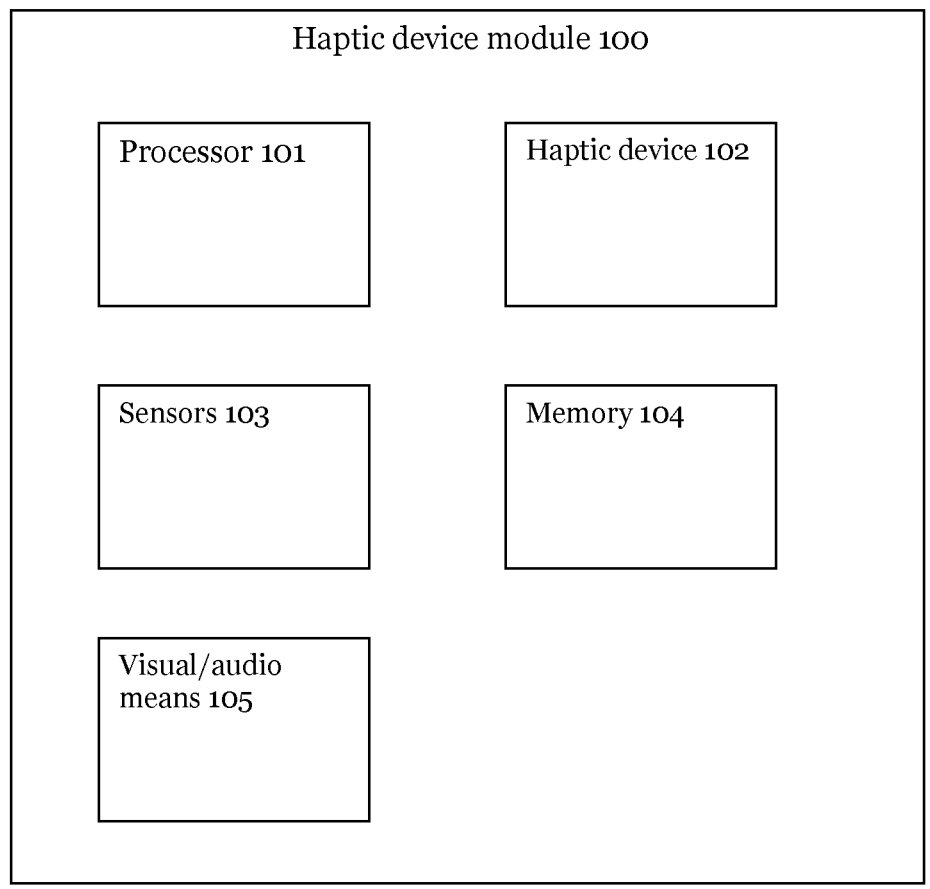
FIG. 1 shows an illustration of a haptic device module in accordance with an embodiment of the invention.

FIG. 1 illustrates a haptic device module 100 in accordance with an embodiment of the invention. The haptic device module 100 comprises processor 101, haptic device 102, sensors 103, memory 104 and visual/audio means 105. Processor 101 can provide instructions for controlling and moving haptic device 102. Haptic device 102 can be a robotic glove or robotic knob. Haptic device 102 can have actuators to supply a force. Haptic device 102 can be powered by a motor. Sensors 103 can be connected to haptic device 102. Sensors 103 can include position encoders which provide position/orientation data of haptic device 102. Sensors 103 can also include force sensors. Sensors 103 feed sensor data and position data into processor 101. Processor 101 can store position data into memory 104. Processor 101 can provide visual or audible instructions to the patient via visual/audio means 105. Visual/audio means 105 can be any display screen or any speaker or the like.

Figure 2A:
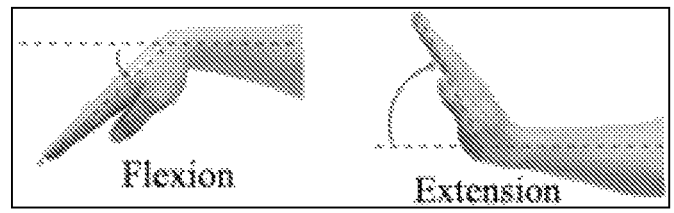
FIG. 2(a) shows an illustration of a finger flexion action and a finger extension action.
Figure 2B:
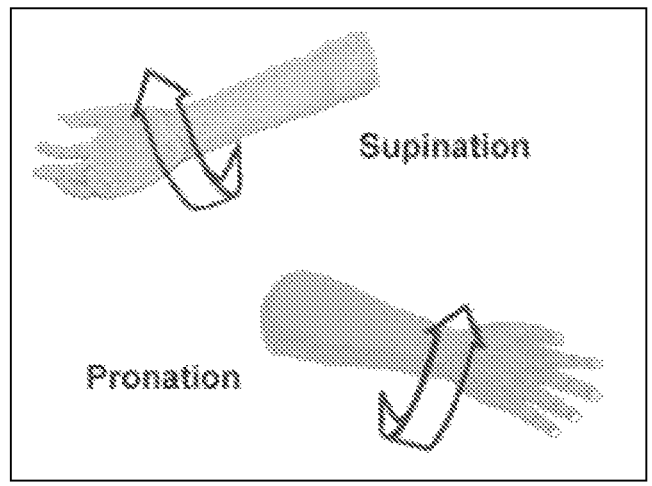
FIG. 2(b) shows an illustration of a forearm supination action and a forearm pronation action.

The method for calibrating haptic device 102 as disclosed involves a patient performing calibration actions. These calibration actions can include a finger flexion action, a finger extension action, a forearm supination action and a forearm pronation action. An illustration of a finger flexion action and a finger extension action is shown in FIG. 2(a) and an illustration of a forearm supination action and a forearm pronation action is shown in FIG. 2(b).

Figure 3:
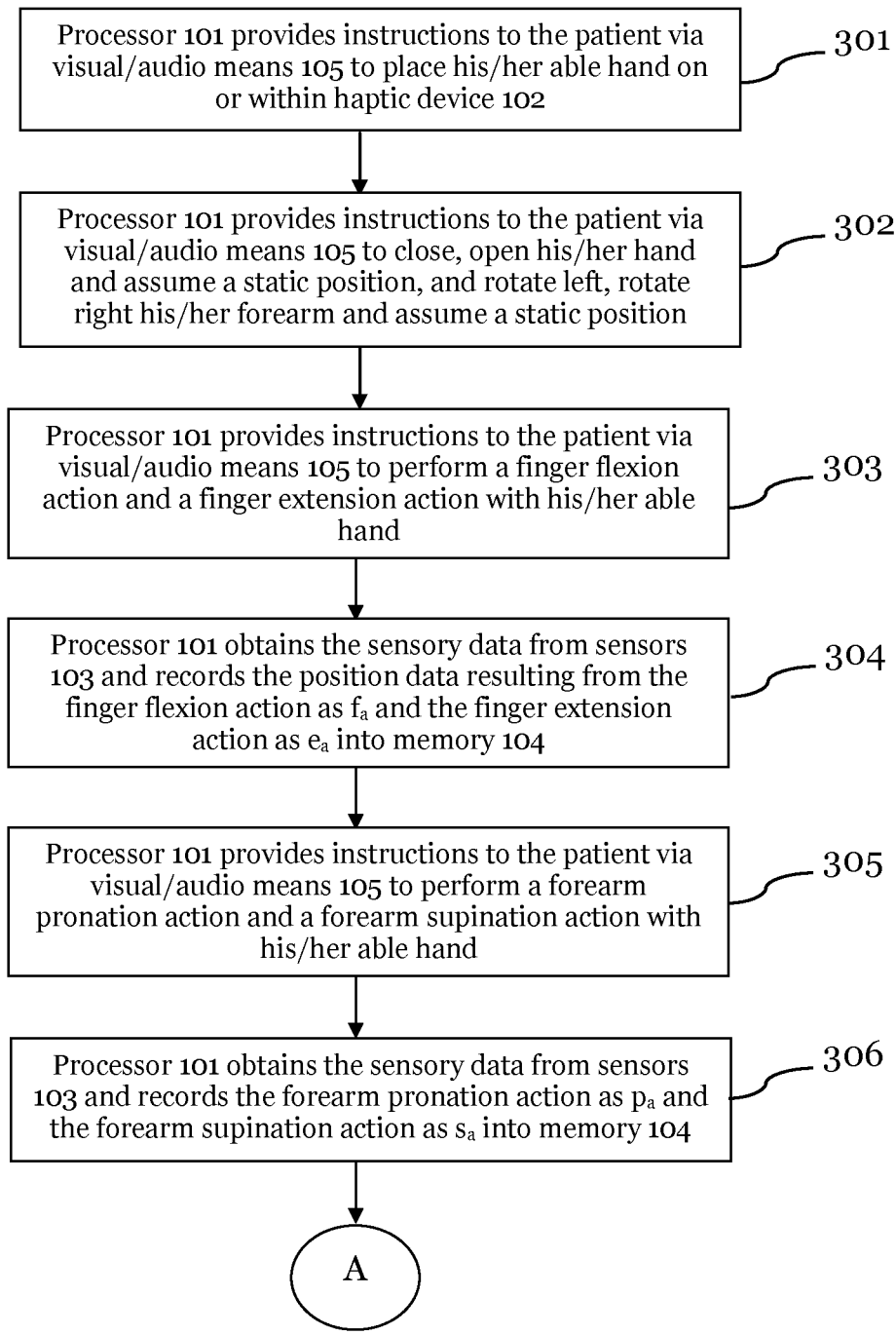
FIG. 3 is a flow chart depicting a method for calibrating a haptic device in accordance with an embodiment of the invention.
Figure 3:
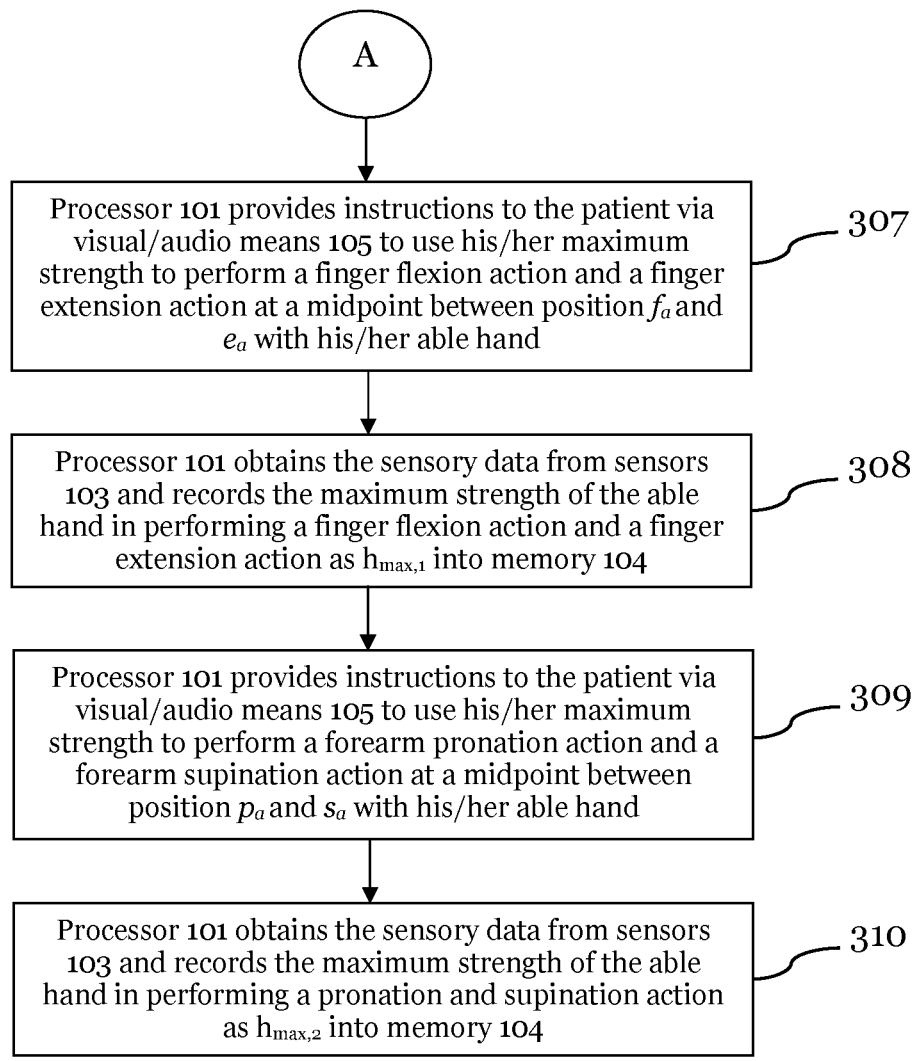
Figure 4:
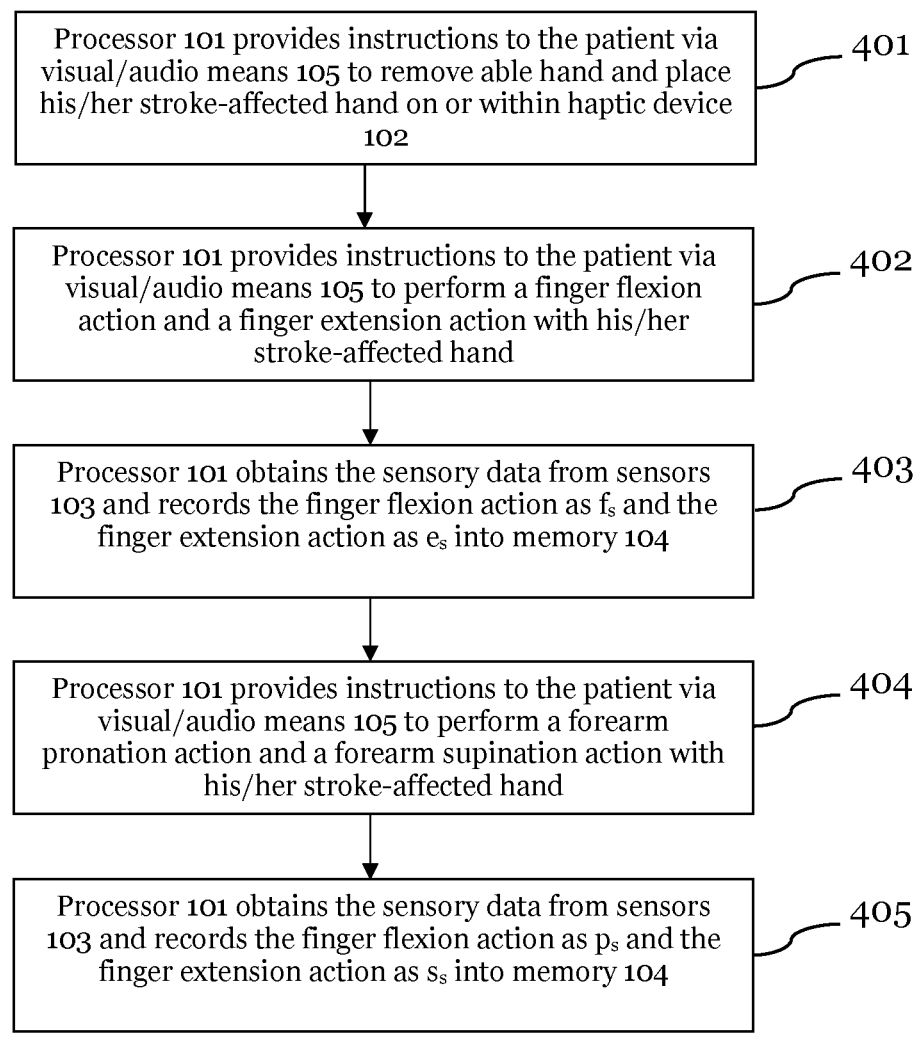
FIG. 4 is a flow chart depicting a method for calibrating a haptic device in accordance with an embodiment of the invention.
Figure 5:
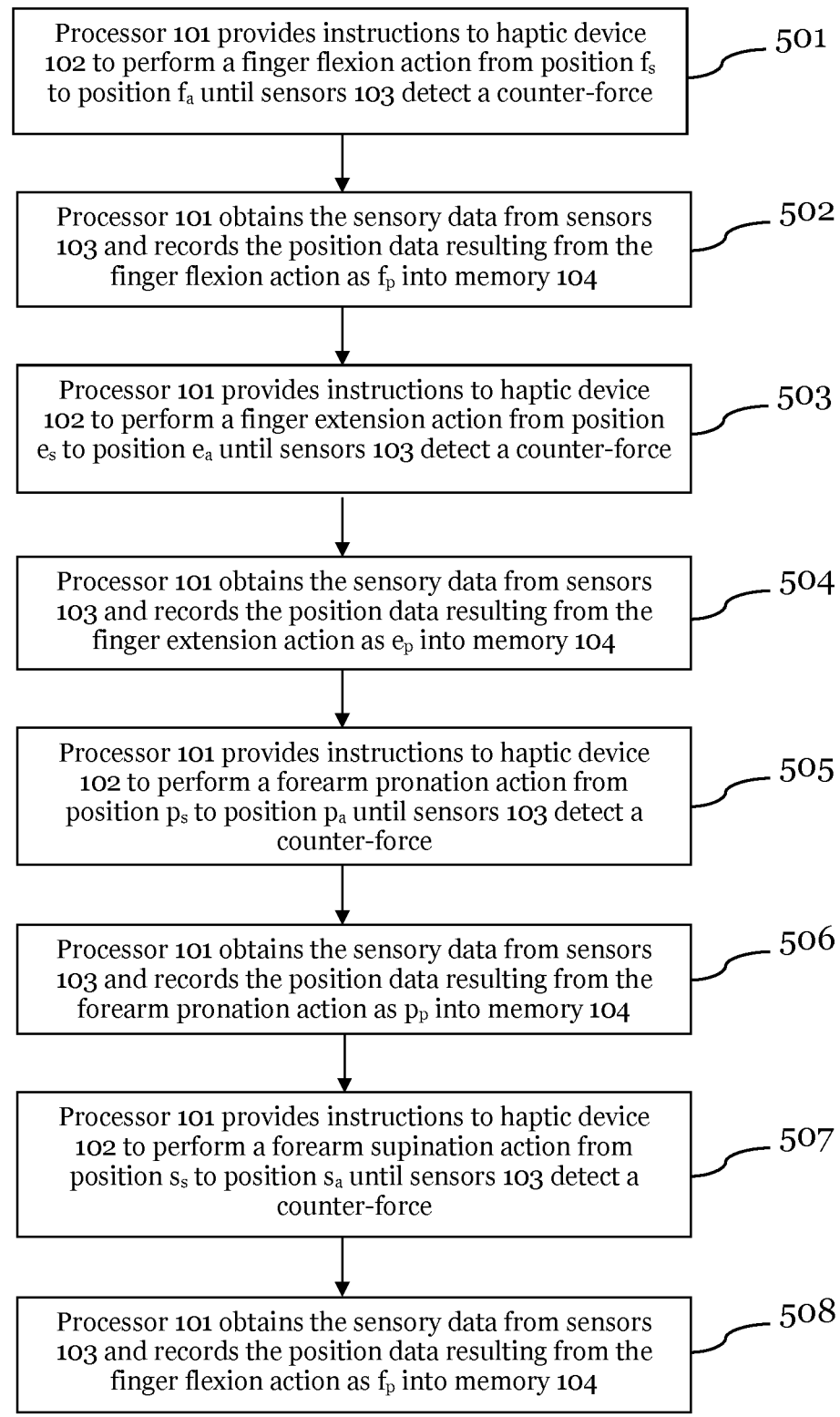
FIG. 5 is a flow chart depicting a method for calibrating a haptic device in accordance with an embodiment of the invention.

FIGS. 3, 4 and 5 are flow charts depicting a method for calibrating haptic device 102 in accordance with an embodiment of the invention.

In step 301 of FIG. 3, processor 101 provides instructions to the patient via visual/audio means 105 to place his/her able hand (un-paralyzed hand) on or within haptic device 102 such that the patient can manipulate haptic device 102 with his/her able hand.

In step 302 of FIG. 3, processor 101 provides instructions to the patient via visual/audio means 105 to close, open his/her hand and assume a resting/static position, and rotate left, rotate right his/her forearm and then assume a resting/static position. The position data of these six positions is saved into memory 104 and this position data will be the initial coordinates of the stroke-affected hand.

In step 303 of FIG. 3, processor 101 provides instructions to the patient via visual/audio means 105 to perform a finger flexion action and a finger extension action with his/her able hand.

In step 304 of FIG. 3, after the actions have been performed, processor 101 obtains the sensory data from sensors 103 and records the position data resulting from the finger flexion action as $f_a$ and the finger extension action as $e_a$ into memory 104.

In step 305 of FIG. 3, processor 101 provides instructions to the patient via visual/audio means 105 to perform a forearm pronation action and a forearm supination action with his/her able hand.

In step 306 of FIG. 3, after the actions have been performed, processor 101 obtains the sensory data from sensors 103 and records the forearm pronation action as $p_a$ and the forearm supination action as $s_a$ into memory 104.

In step 307 of FIG. 3, processor 101 provides instructions to the patient via visual/audio means 105 to use his/her maximum strength to perform a finger flexion action and a finger extension action at a midpoint between position $f_a$ and $e_a$ with his/her able hand. The midpoint is a position where the patient's hand is at rest and not exerting any muscle force. It is not necessarily the half point between the maximum finger flexion and maximum finger extension. It is just the position whereby the patient's hand is comfortably relaxed and at rest. In essence, the patient is asked to exert maximum force with his able hand from a stationary position.

In step 308 of FIG. 3, after the actions have been performed, processor 101 obtains the sensory data from sensors 103 and records the maximum strength of the able hand in performing a finger flexion action and a finger extension action as $h_{max,1}$ into memory 104.

In step 309 of FIG. 3, processor 101 provides instructions to the patient via visual/audio means 105 to use his/her maximum strength to perform a forearm pronation action and a forearm supination action at a midpoint between position $p_a$ and $s_a$ with his/her able hand. The midpoint is a position where the patient's hand is at rest and not exerting any muscle force. It is not necessarily the half point between the maximum pronation and maximum supination. It is just the position whereby the patient's hand is comfortably relaxed and at rest.

In step 310 of FIG. 3, after the actions have been performed, processor 101 obtains the sensory data from sensors 103 and records the maximum strength of the able hand in performing a pronation and supination action as $h_{max,2}$ into memory 104.

It is to be noted that the manipulation of haptic device 102 by the patient through steps 301 to 310 is unassisted (no force is applied by haptic device 102) and is done entirely by the patient's able hand.

In step 401 of FIG. 4, processor 101 provides instructions to the patient via visual/audio means 105 to remove able hand and place his/her stroke-affected hand (paralyzed hand) on or within haptic device 102 such that the patient can manipulate haptic device 102 with his/her stroke-affected hand.

In step 402 of FIG. 4, processor 101 provides instructions to the patient via visual/audio means 105 to perform a finger flexion action and a finger extension action with his/her stroke-affected hand.

In step 403 of FIG. 4, after the actions have been performed, processor 101 obtains the sensory data from sensors 103 and records the finger flexion action as $f_s$ and the finger extension action as $e_s$ into memory 104.

In step 404 of FIG. 4, processor 101 provides instructions to the patient via visual/audio means 105 to perform a forearm pronation action and a forearm supination action with his/her stroke-affected hand.

In step 405 of FIG. 4, after the actions have been performed, processor 101 obtains the sensory data from sensors 103 and records the finger flexion action as $p_s$ and the finger extension action as $s_s$ into memory 104.

It is to be noted that the manipulation of haptic device 102 by the patient through steps 401 to 405 is unassisted (no force is applied by haptic device 102) and is done entirely by the patient's stroke-affected hand.

In step 501 of FIG. 5, processor 101 provides instructions to haptic device 102 to perform a finger flexion action from position $f_s$ to position $f_a$ (the patient's stroke-affected hand will move along with haptic device 102 as they are still coupled together at this juncture) until sensors 103 detect a counter-force as a result of the patient's stroke-affected hand resistance to movement. Preferably, the counterforce is larger than one quarter of the maximum strength of the able hand in performing a finger flexion action and a finger extension action $h_{max,1}$, i.e. counter force >0.25 $h_{max,1}$.

In step 502 of FIG. 5, processor 101 obtains the sensory data from sensors 103 and records the position data resulting from the finger flexion action as $f_p$ into memory 104. $f_p$ therefore represents the extreme position in which the patient can flex his/her fingers with his/her stroke-affected hand without causing the patient excruciating pain and yet providing the necessary leeway for improvement in his/her stroke-affected hand.

In step 503 of FIG. 5, processor 101 provides instructions to haptic device 102 to perform a finger extension action from position $e_s$ to position $e_a$ (the patient's stroke-affected hand will move along with haptic device 102 as they are still coupled together at this juncture) until sensors 103 detect a counter-force as a result of the patient's stroke-affected hand resistance to movement. Preferably, the counterforce is larger than one quarter of the maximum strength of the able hand in performing a finger flexion action and a finger extension action $h_{max,1}$, i.e. counter force >0.25 $h_{max,1}$.

In step 504 of FIG. 5, processor 101 obtains the sensory data from sensors 103 and records the position data resulting from the finger extension action as $e_p$ into memory 104. $e_p$ therefore represents the extreme position in which the patient can extend his/her fingers with his/her stroke-affected hand without causing the patient excruciating pain and yet providing the necessary leeway for improvement in his/her stroke-affected hand.

In step 505 of FIG. 5, processor 101 provides instructions to haptic device 102 to perform a forearm pronation action from position $p_s$ to position $p_a$ (the patient's stroke-affected hand will move along with haptic device 102 as they are still coupled together at this juncture) until sensors 103 detect a counter-force as a result of the patient's stroke-affected hand resistance to movement. Preferably, the counterforce is larger than one quarter of the maximum strength of the able hand in performing a pronation and supination action $h_{max,2}$, i.e. counter force >0.25 $h_{max,2}$.

In step 506 of FIG. 5, processor 101 obtains the sensory data from sensors 103 and records the position data resulting from the forearm pronation action as $p_p$ into memory 104. $p_p$ therefore represents the extreme position in which the patient can pronate his/her forearm with his/her stroke-affected hand without causing the patient excruciating pain and yet providing the necessary leeway for improvement in his/her stroke-affected hand.

In step 507 of FIG. 5, processor 101 provides instructions to haptic device 102 to perform a forearm supination action from position $s_s$ to position $s_a$ (the patient's stroke-affected hand will move along with haptic device 102 as they are still coupled together at this juncture) until sensors 103 detect a counter-force as a result of the patient's stroke-affected hand resistance to movement. Preferably, the counterforce is larger than one quarter of the maximum strength of the able hand in performing a pronation and supination action $h_{max,2}$, i.e. counter force >0.25 $h_{max,2}$.

In step 508 of FIG. 5, processor 101 obtains the sensory data from sensors 103 and records the position data resulting from the forearm pronation supination as $s_p$ into memory 104. $s_p$ therefore represents the maximum position or extent in which the patient can supinate his/her forearm with his/her stroke-affected hand without causing the patient excruciating pain and yet providing the necessary leeway for improvement in his/her stroke-affected hand.

Figure 6:
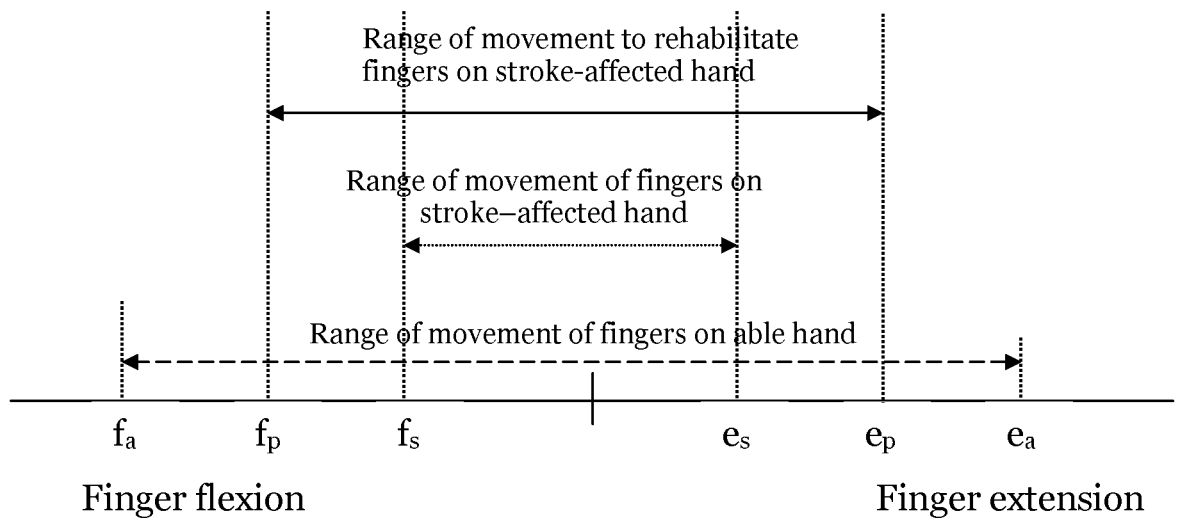
FIG. 6 shows an illustration of the range of movement for rehabilitating a finger on the patient's stroke-affected hand.
Figure 7:
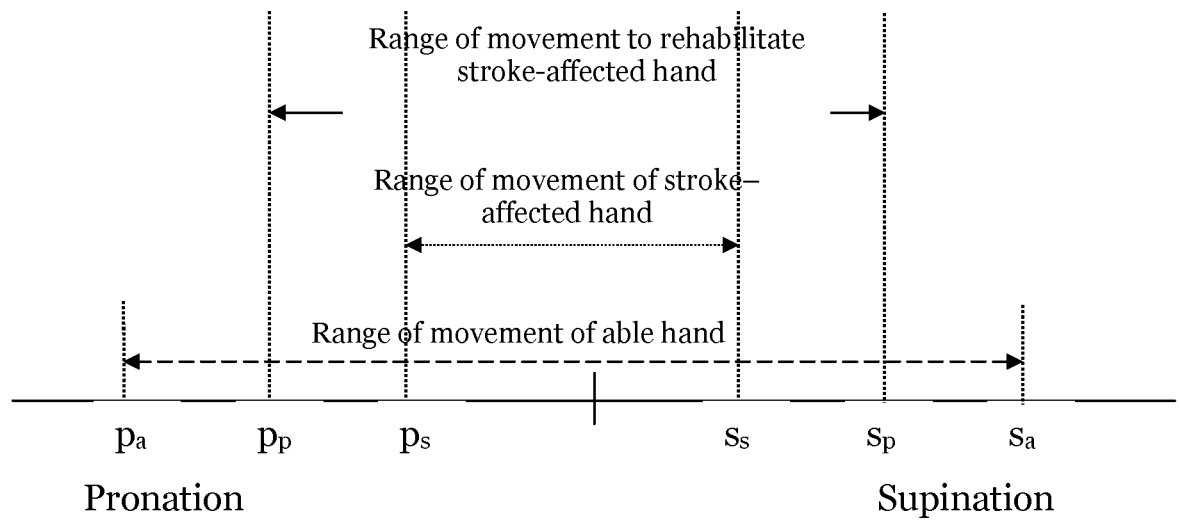
FIG. 7 shows an illustration of the range of movement for rehabilitating the patient's stroke-affected hand.

The range of movement to rehabilitate the fingers of the patient's stroke-affected hand is therefore determined i.e. $f_p$ for the finger flexion action and $e_p$ for the finger extension action. The range of movement to rehabilitate the fingers of the patient's stroke-affected hand is illustrated in FIG. 6. The range of movement to rehabilitate the patient's stroke-affected hand is therefore determined i.e. $p_p$ for the pronation action and $s_p$ for the supination action. The range of movement to rehabilitate the patient's stroke-affected hand is illustrated in FIG. 7.

Once memory 104 has stored $f_p$ for the finger flexion action, $e_p$ for the finger extension action, $p_p$ for the pronation action and $s_p$ for the supination action, haptic device 102 is successfully calibrated and configured for the patient. $f_p$, $e_p$, $p_p$ and $s_p$ represent the extreme positions for the stroke-affected hand when using haptic device 102 for the rehabilitation exercises. In other words, during the rehabilitation exercises, the haptic device 102 would not move beyond these extreme positions. These extreme positions represent the ideal upper limit for the rehabilitation exercises. Any position before or below these extreme positions mean that the stroke-affected hand still has room for improvement, while any position beyond these extreme positions will cause the patient excruciating pain. The calibration process is advantageous because it can automatically determine the extreme positions which haptic device 102 can assume when the patient undergoes the rehabilitation exercises.

The calibration process is also advantageous because it is automatic and does not require a therapist, thereby reducing manpower costs. Further, as the calibration process is computerized with sensors 103 providing the necessary feedback, this calibration process is not subject to human error. Furthermore, the calibration process is robust enough to accommodate patients with varying hand sizes as well as right handed and left handed individuals. Obviously, for varying hand sizes, the range of movement and extreme positions will be different.

Figure 8:
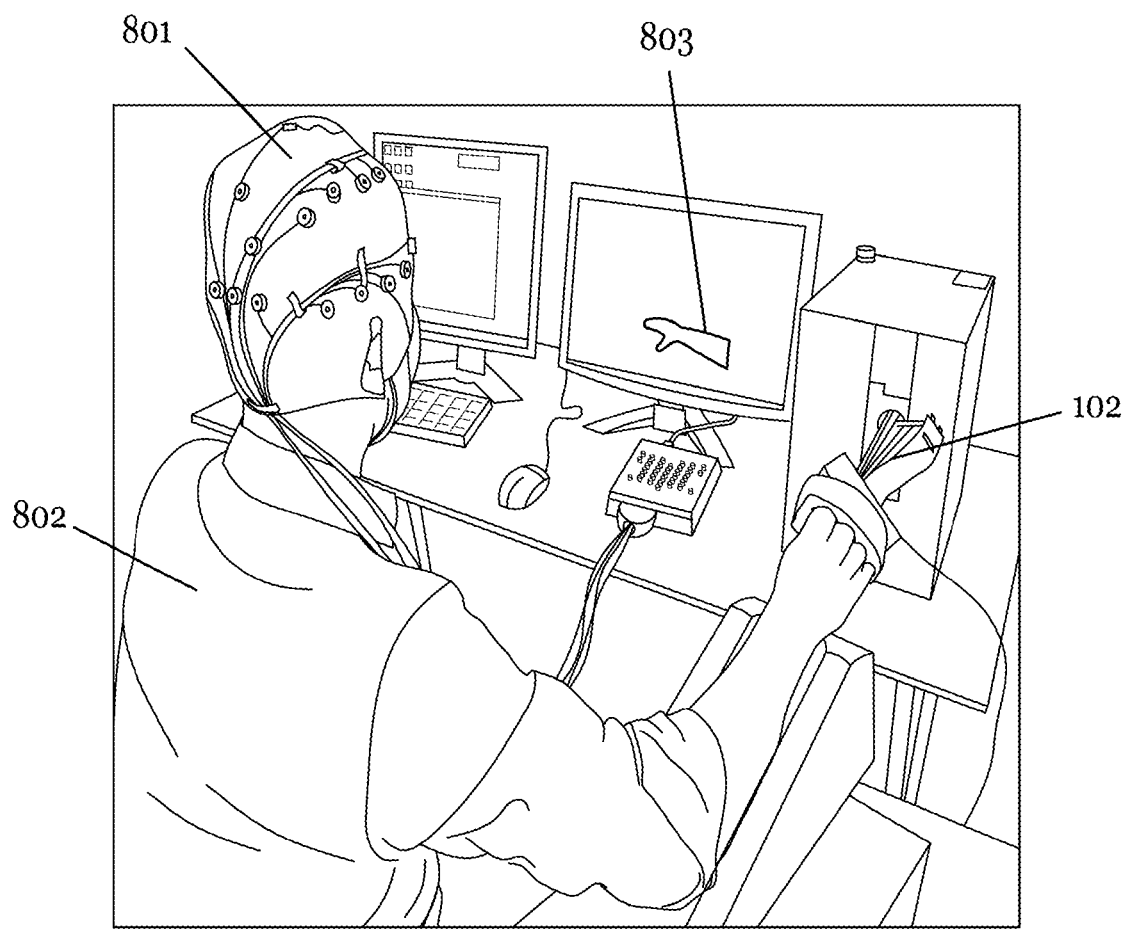
FIG. 8 illustrates a patient undergoing the rehabilitation exercises.

After the calibration of haptic device 102, the patient can begin the rehabilitation exercises. FIG. 8 illustrates a patient undergoing the rehabilitation exercises. FIG. 8 shows an electroencephalogram (EEG) headset 801 on patient's 802 head. Patient's 802 stroke-affected hand is placed on or within haptic device 102. EEG headset 801 measures patient's 802 brain signals. The image of a moving hand is shown on screen 803. This image provides the visual cue for patient 802 to perform motor imagery i.e. imagining moving his stroke-affected hand. During this time, patient 802 is unable to move or manipulate haptic device 102 due to a resistive force being applied by a motor of haptic device 102.

Once motor imaginary is successfully detected, patient 802 can then perform the rehabilitation exercises which can include finger flexion, finger extension, forearm pronation and forearm supination exercises. To supplement these rehabilitation exercises, screen 803 can display a virtual simulation which mirrors the rehabilitation exercises being performed by patient 802.

In an embodiment of the invention, haptic device 102 executes or helps executes the rehabilitation exercises by applying an assistive force or resistive force when necessary. This assistive force or resistive force is denoted as α. When a is a positive value (+ve), haptic device 102 provides an assistive force to aid patient 802 in performing the exercises. When a is a negative value (−ve), haptic device 102 provides a resistive force to prevent patient 802 from overexerting himself/herself during the exercises. Assistive force/resistive force α can be a function of the hand strength of stroke-affected hand h, maximum hand strength of the able hand $h_{max}$ ($h_{max,1}$ if it is a finger flexion and extension exercise, and $h_{max,2}$ if it is a forearm pronation and supination exercise), motor imagery score m, and maximum motor imagery score $m_{max}$. $m_{max}$ is typically 100. The reason why assistive/resistive force α is dependent on the maximum hand strength $h_{max}$ is because different patients have different hand strength. So instead of setting assistive force/resistive force α to a fixed value, it is advantageous to account for the varying hand strength of patients by making assistive force/resistive force α dependent on the hand strength of the patient 802. The maximum strength of patient's 802 stroke-affected hand is more or less the same as the maximum strength of his able hand. Therefore, the maximum strength of patient's 802 able hand is used as an approximation of the maximum strength of his stroke-affected hand.

Assistive force/resistive force α can therefore be presented as:

$$\alpha = -\tanh\left(\frac{5}{h_{max}}\left(h - \frac{h_{max}}{2}\right)\right)\tanh\left(\frac{5m}{m_{max}}\right)$$

Figure 9:
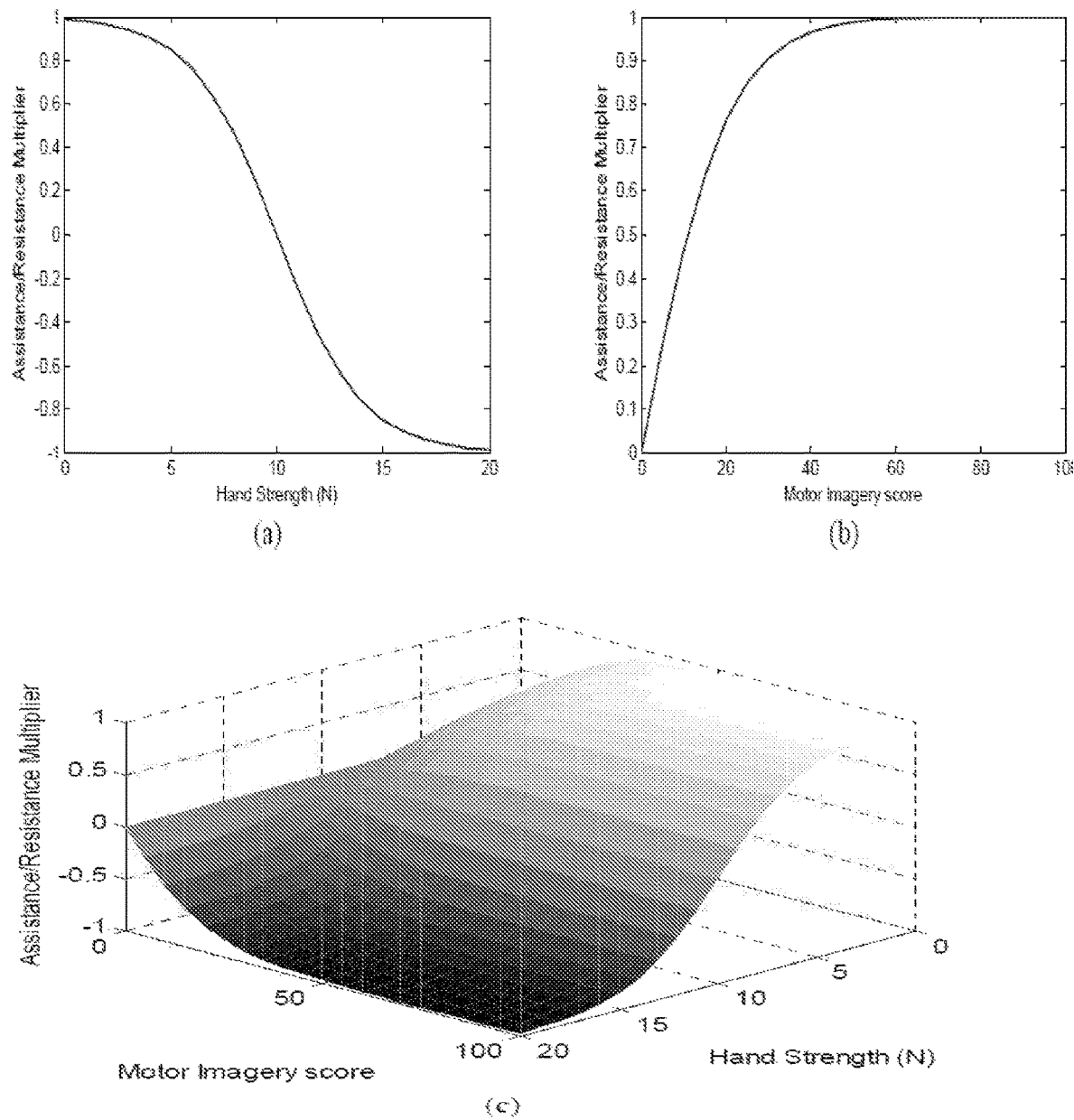
FIG. 9(a) shows a graph of assistive force/resistive force applied by haptic device plotted against hand strength of stroke-affected hand.
FIG. 9(b) shows a graph of assistive force/resistive force applied by haptic device plotted against motor imagery score of the patient.
FIG. 9(c) shows a graph that plots the change in assistive force/resistive force applied by haptic device against motor imagery score of the patient and hand strength of stroke-affected hand.

FIG. 9(a) shows a graph of assistive force/resistive force α applied by haptic device 102 plotted against hand strength of the stroke-affected hand h. The relationship between hand strength of the stroke-affected hand h and assistive force/resistive force α applied by haptic device 102 is that if patient 802 uses very little hand strength with his/her stroke-affected hand when performing the rehabilitation exercise, α becomes a positive value and haptic device 102 applies an assistive force α to aid patient 802 in the rehabilitation exercise.

However, if patient 802 applies a significant amount of hand strength with his/her stroke-affected hand when performing the rehabilitation exercise, α becomes a negative value and haptic device 102 applies a resistive force α to slow down the movement of patient 802 stroke-affected hand, thereby increasing the effort patient 802 has to exert on his/her stroke-affected hand during the rehabilitation exercise. This is advantageous as existing haptic systems provides only an assistive force, and not a resistive force. The haptic device 102 as described herein therefore contemplates a scenario where patient 802 may be able to move his/her stroke-affected hand, which in this case the haptic device 102 applies a resistive force α and moving against this resistive force helps patient 802 to gain further strength on the stroke-affected hand. In other words, if patient 802 is capable of moving his/her stroke-affected hand, one of the objectives of the rehabilitation exercises would be to make patient 802 exert even more force. Therefore, a resistive force is applied so that patient 802 can be trained to exert even more effort. This is similar in concept to weight training Once a person can move a certain amount of weights, the training will progress on to heavier weights.

FIG. 9(b) shows a graph of assistive force/resistive force α applied by haptic device 102 plotted against motor imagery score m. A low motor imagery score means that patient 802 is unable to properly imagine or visualize moving his/her stroke-affected hand while a high motor imagery score means that patient 802 is able to properly imagine or visualize moving his/her stroke-affected hand. Motor imagery score m and assistive force α have a directly proportional relationship in that the higher the motor imagery score m obtained by patient 802, the greater the assistive force α applied by haptic device 102 to aid patient 802 in the exercise. This is advantageous because the better patient 802 can visualize moving his/her stroke-affected hand (i.e. higher motor imagery score), the further patient 802 can push or extend himself/herself during the rehabilitation exercises. Therefore, haptic device 102 applies a larger assistive force α to increase the speed of movement during the rehabilitation exercises. The disability of patient 802 is usually tied to his/her volition, willpower and effort. The more involved a patient is, or the more effort the patient imagines the motor imagery, the more assistive movement is provided to make the intensity of the rehabilitation exercises coincide with the effort put forth. The invention therefore capitalizes on the correlation between effort and the intensity of the rehabilitation exercises to enhance the effectiveness of the rehabilitation process.

FIG. 9(c) shows a graph that plots the change in assistive force/resistive force α against motor imagery score m and hand strength h.

The hand strength of the stroke-affected hand h exerted by patient 802 when performing the rehabilitation exercises can be evaluated by measuring the force applied to sensors 103. However, sometimes sensors 103 can be cumbersome due to the additional wiring. Therefore preferably, hand strength of the stroke-affected hand h is measured by measuring the driving motor current necessary to maintain the same servo motor position. The linear relationship between the applied force F and the driving motor current I is given by:

$$I = kcF + I_0,$$

and therefore $$F = \frac{I - I_0}{kc},$$

where k is the transferring factor of the applied to the analogous current output of the motor for hand grasping movement, c is the conversion factor of the analog-to-digital (AD) convertor of the driving motor, and $I_0$ is a constant caused by inertia and friction of the mechanism.

Therefore, the hand strength of the stroke-affected hand applied during the rehabilitation exercises is therefore:

$$F_i = \frac{1}{n}\sum_{j=1}^{n} F_{i,j}$$

where $F_i$ is the average hand strength of the stroke-affected hand for the $i^{th}$ rehabilitation exercise, $F_{i,j}$ is the actively evaluated hand strength of the stroke-affected hand for the $j^{th}$ rehabilitation exercise.

Figure 10:
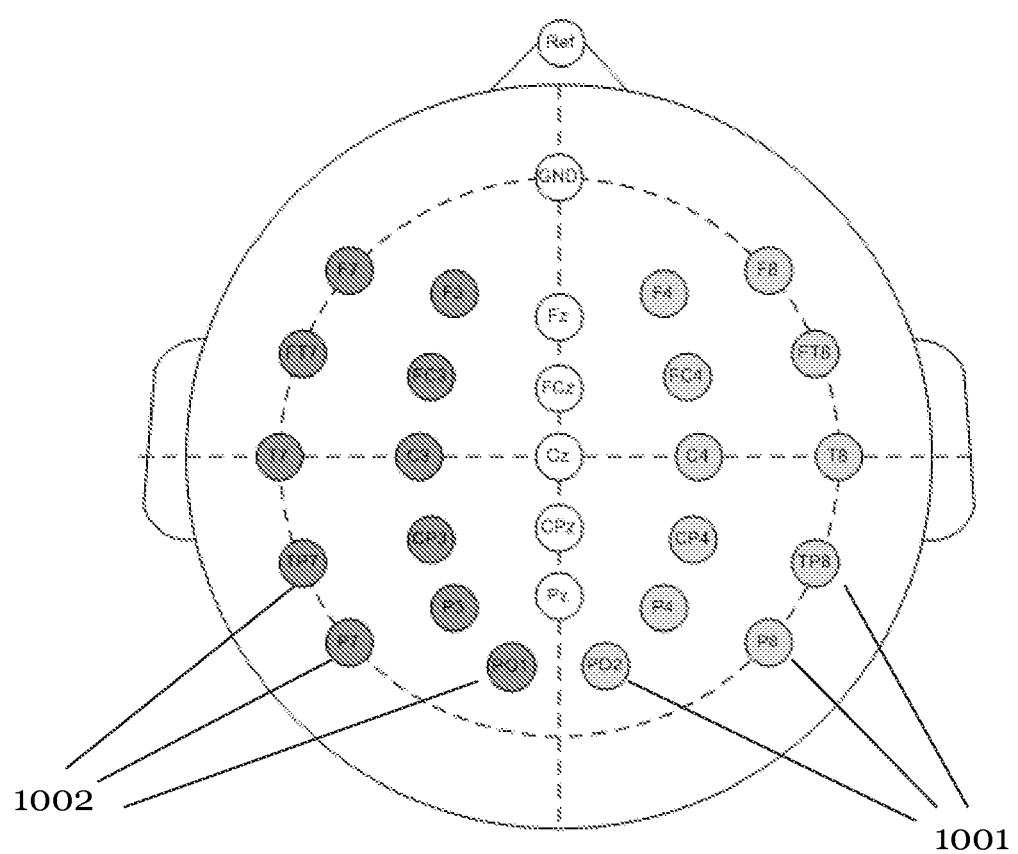
FIG. 10 shows the locations of the channel electrodes on the brain.

In another embodiment of the invention, the EEG data collected during the rehabilitation exercises can be used to compute the Temporal Spectral-dependent Brain Index (TSBI). TSBI can be computed using the following equation:

$$TSBI(t) = \frac{1}{n_k}\sum_{n=k_1}^{k_2} \left|\frac{R_n^*(t) - L_n^*(t)}{R_n^*(t) + L_n^*(t)}\right|,$$

where $$R_n^*(t) = \frac{1}{n_c}\sum_{c=1}^{n_c} a_n^2(c, t)$$

evaluates the averaged Fourier coefficient of eleven channel electrodes 1001 taken from the right hemisphere of the brain as shown in FIG. 10 (i.e. $n_c$=11);
and where $$L_n^*(t) = \frac{1}{n_c}\sum_{c=1}^{n_c} a_n^2(c, t)$$

evaluates the averaged Fourier coefficient of eleven channel electrodes 1002 taken from the left hemisphere of the brain as shown in FIG. 10 (i.e. $n_c$=11);
and where $a_n(c,t)$ is the Fourier coefficient of index n of channel electrode c evaluated at time t that corresponds to a particular time segment [t−T, t], with T being the duration in which the motor imagery is being performed;
and where the Fourier coefficients [$k_1$ and $k_2$] corresponds to the frequency band [4-40 Hz] evaluated by the brain-computer interface (BCI) for performing motor imagery, and $n_k$ is the number of Fourier coefficients evaluated that correspond to the frequency band [4-40 Hz].

Figure 11:
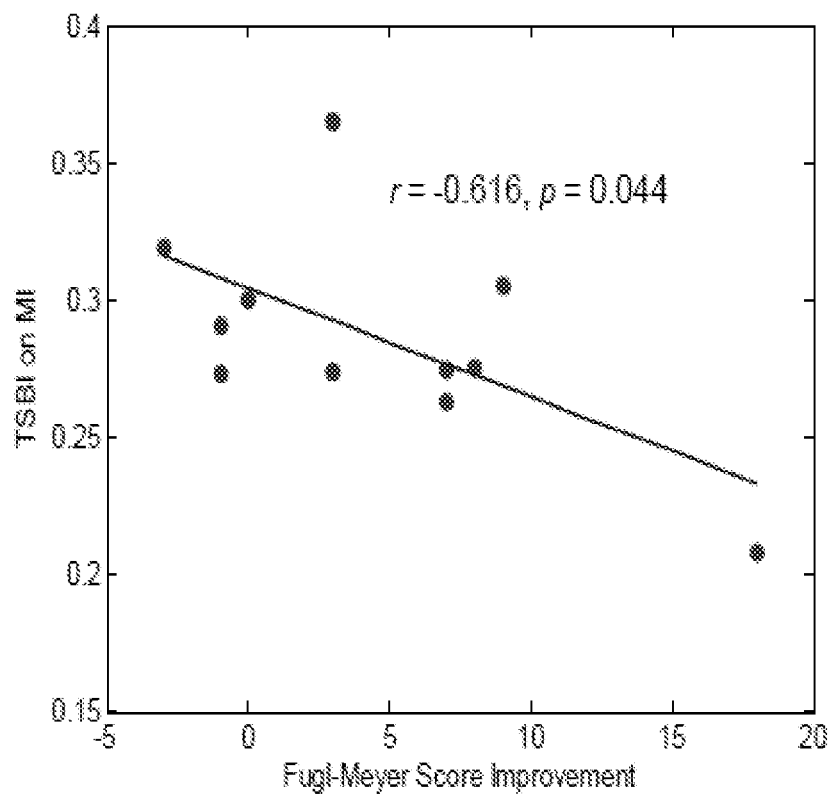
FIG. 11 shows a graph of Temporal Spectral-dependent Brain Indexes (TSBI) plotted against Fugi-Meyer Score Improvement.

Preferably, TSBI can be used as a prognostic measure to predict the possible outcome of the rehabilitation. When TSBIs are plotted against Fugi-Meyer Score Improvement, the results show that a lower TSBI resulted in a higher Fugi-Meyer Score Improvement. See FIG. 11 which plots a graph of TSBIs calculated using motor imagery (MI) against Fugi-Meyer Score Improvement. Therefore, this shows that TSBI can be used to predict the progress of stroke rehabilitation.

Although all the embodiments of the invention have been described with the rehabilitation of a stroke-affected hand, forearm or wrist, one skilled in the art will appreciate that the invention can be applied to rehabilitate other stroke-affected limbs, for example, a stroke-affected leg.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A method for calibrating and executing a rehabilitation exercise for a stroke-affected limb of a stroke patient, the stroke patient having an able limb, the method comprising:
providing a haptic device for the able limb to manipulate;
providing with a screen, automated visual/audio instructions to guide the stroke patient in using the able limb to manipulate the haptic device to perform at least one calibration action;
determining a first position of the haptic device, the first position resultant from the manipulation of the haptic device by the able limb in completing the at least one calibration action;
providing the haptic device for the stroke-affected limb to manipulate;
providing with the screen, automated visual/audio instructions to guide the stroke patient in using the stroke-affected limb to manipulate the haptic device to perform the at least one calibration action;
determining a second position of the haptic device, the second position resultant from the manipulation of the haptic device by the stroke-affected limb in completing the at least one calibration action;
moving the haptic device coupled with the stroke-affected limb from the second position towards the first position until a predetermined counterforce emanating from the stroke-affected limb is detected, indicating an extreme position for the stroke-affected limb using the haptic device; and
calibrating the haptic device with the extreme position such that during the rehabilitation exercise for the stroke-affected limb, the haptic device is prevented from moving beyond the extreme position,
wherein a force applied by the haptic device is a function of a motor imagery score of the stroke patient, a limb strength of the stroke-affected limb and a maximum limb strength of the able limb, and
wherein the force applied by the haptic device is represented by an equation $$\alpha = -\tanh\left(\frac{5}{h_{max}}\left(h - \frac{h_{max}}{2}\right)\right)\tanh\left(\frac{5m}{m_{max}}\right),$$

wherein α is the force applied by the haptic device, h is the limb strength of the stroke-affected limb, hmax is the maximum limb strength of the able limb, m is the motor imagery score of the stroke patient, and mmax is a maximum motor imagery score.

2. The method of claim 1 wherein the rehabilitation exercise has the same sequence of movements as the at least one calibration action.

3. The method of claim 1 wherein the at least one calibration action is any one of, or any combination of the following actions: finger flexion, finger extension, forearm pronation and forearm supination.

4. The method of claim 1 further comprising:
providing with the screen, automated visual/audio instructions to guide the stroke patient in using the able limb to apply maximum strength when the haptic device is stationary; and
determining the maximum limb strength of the able limb by measuring the maximum strength applied by the able limb.

5. The method of claim 4 wherein the predetermined counterforce is greater than one quarter of the maximum limb strength of the able limb.

6. The method of claim 4 further comprising the operation of determining a limb strength of the stroke-affected limb by measuring the driving motor current necessary to maintain the same servo motor position during the rehabilitation exercise for the stroke-affected limb.

7. The method of claim 6 further comprising the operation of using a brain computer interface (BCI) system to obtain electroencephalogram (EEG) data from the brain of the stroke patient, and determining from the EEG data, a motor imagery score of the stroke patient.

8. The method of claim 7 further comprising the operation of executing the rehabilitation exercise for the stroke-affected limb by applying the force with the haptic device.

9. The method of claim 8 wherein the force applied by the haptic device is an assistive force or a resistive force depending on the limb strength of the stroke-affected limb.

10. The method of claim 7 further comprising the operation of using the EEG data to compute a Temporal Spectral-dependent Brain Index (TSBI), and then plotting the TSBI against Fugi-Meyer Score Improvement in a graph so as to predict the progress of stroke rehabilitation.

11. The method of claim 10 wherein the TSBI is calculated using the equation $$TSBI(t) = \frac{1}{n_k} \sum_{n=k_1}^{k_2} \left| \frac{R_n^*(t) - L_n^*(t)}{R_n^*(t) + L_n^*(t)} \right|.$$

12. A system for calibrating and executing a rehabilitation exercise for a stroke-affected limb of a stroke patient, the stroke patient having an able limb, the system comprising a haptic device, a screen, at least one sensor and a processor;
wherein the haptic device is capable of:
being manipulated by the able limb, in response to automated visual/audio instructions provided by the screen to guide the stroke patient in using the able limb to manipulate the haptic device to perform at least one calibration action, wherein the at least one sensor is configured to determine a first position of the haptic device, the first position resultant from the manipulation of the haptic device by the able limb in completing the at least one calibration action;
being manipulated by the stroke-affected limb, in response to automated visual/audio instructions provided by the screen to guide the stroke patient in using the stroke-affected limb to manipulate the haptic device to perform the at least one calibration action; wherein the at least one sensor is configured to determine a second position of the haptic device, the second position resultant from the manipulation of the haptic device by the stroke-affected limb in completing the at least one calibration action; and
moving, coupled with the stroke-affected limb, from the second position towards the first position until a predetermined counterforce emanating from the stroke-affected limb is detected by the least one sensor, indicating an extreme position for the stroke-affected limb using the haptic device;
wherein the processor is configured to calibrate the haptic device with the extreme position such that during the rehabilitation exercise for the stroke-affected limb, the haptic device is prevented from moving beyond the extreme position,
wherein a force applied by the haptic device is a function of a motor imagery score of the stroke patient, a limb strength of the stroke-affected limb and a maximum limb strength of the able limb, and
wherein the force applied by the haptic device is represented by an equation $$\alpha = -\tanh\left(\frac{5}{h_{max}}\left(h - \frac{h_{max}}{2}\right)\right)\tanh\left(\frac{5m}{m_{max}}\right),$$

wherein $\alpha$ is the force applied by the haptic device, h is the limb strength of the stroke-affected limb, hmax is the maximum limb strength of the able limb, m is the motor imagery score of the stroke patient, and mmax is a maximum motor imagery score.

13. The system of claim 12 wherein the haptic device is a glove that fits onto a hand of the stroke patient.

14. The system of claim 12 wherein the at least one sensor comprises position encoders for providing position and orientation data of the haptic device.

15. The system of claim 12 further comprising a brain computer interface (BCI) system, the BCI system configured to obtain electroencephalogram (EEG) data from a brain of the stroke patient, and determine from the EEG data the motor imagery score of the stroke patient.

16. The system of claim 15 wherein the haptic device is configured to execute the rehabilitation exercise by applying the force during the rehabilitation exercise for the stroke-affected limb, wherein the force is a function of the motor imagery score of the stroke patient, the limb strength of the stroke-affected limb and the maximum limb strength of the able limb.

17. The system of claim 16 wherein the force applied by the haptic device is an assistive force or a resistive force depending on the limb strength of the stroke-affected limb.

18. The system of claim 15 wherein the EEG data is used to compute a Temporal Spectral-dependent Brain Index (TSBI), and the TSBI is then plotted against Fugi-Meyer Score Improvement in a graph so as to predict progress of stroke rehabilitation.

* * * * *